(12) United States Patent
Sheng et al.

(10) Patent No.: US 7,527,974 B2
(45) Date of Patent: May 5, 2009

(54) EMBRYONIC STEM CELLS DERIVED FROM HUMAN SOMATIC CELL—RABBIT OOCYTE NT UNITS

(75) Inventors: Huizhen Sheng, 100/545 Zhenning Road, Shanghai 200000 (CN); Ying Chen, Shanghai (CN); Kai Wang, Shanghai (CN); Ailian Liu, Shanghai (CN)

(73) Assignees: Shanghai Second Medical University, Shanghai (CN); Huizhen Sheng, Shanghai (CN)

( * ) Notice: Subject to any disclaimer, the term of this patent is extended or adjusted under 35 U.S.C. 154(b) by 369 days.

(21) Appl. No.: 10/494,074

(22) PCT Filed: Nov. 6, 2001

(86) PCT No.: PCT/CN01/01536

§ 371 (c)(1),
(2), (4) Date: Oct. 12, 2004

(87) PCT Pub. No.: WO03/040358

PCT Pub. Date: May 15, 2003

(65) Prior Publication Data

US 2005/0064586 A1  Mar. 24, 2005

(51) Int. Cl.
C12N 5/02 (2006.01)
C12N 5/08 (2006.01)
C12N 15/00 (2006.01)

(52) U.S. Cl. .................. 435/377; 435/366; 800/24

(58) Field of Classification Search .............. 435/366, 435/377; 800/24
See application file for complete search history.

(56) References Cited

U.S. PATENT DOCUMENTS 5,945,577 A * 8/1999 Stice et al. .................. 800/24

FOREIGN PATENT DOCUMENTS

| WO | 98/07841 | 2/1998 |
|----|----------|--------|
| WO | 99/45100 | 9/1999 |
| WO | 00/52145 | 9/2000 |

OTHER PUBLICATIONS

Collas et al. Factors Affecting the Efficiency of Nuclear Transplantation in the Rabbit Embryo. Biol. Reprod., vol. 43, pp. 877-884.*
Kawase et al. Mouse Embryonic Stem (ES) Cell Lines Established from Neuronal Cell-Derived Cloned Blastocyts. Genesis, vol. 28, pp. 156-163.*
Schoonjans et al. Pluripotential Rabbit Embryonic Stem (ES) Cells are Capable of Forming Overt Coat Color Chimeras Following Injection Into Blastocysts. Molec. Reprod. Develop. 1996, vol. 45, pp. 439-443.*
Du et al. Nuclear Transfer of Putative Rabbit Embyronic Stem Cells Leads to Normal Blastocyst Development. J. Reprod. Fertil. 1995, vol. 104, pp. 219-223.*

* cited by examiner

Primary Examiner—Deborah Crouch
(74) Attorney, Agent, or Firm—Ladas and Parry LLP

(57) ABSTRACT

The present invention discloses a process for obtaining somatic cell derived embryonic stem cells (encoded by reprogrammed somatic cell nuclei), ES cell-like cells or other types of embryo-derived stem cells by nuclear transplantation, and a process for inducing said stem cells into various differentiated cell types.

17 Claims, 6 Drawing Sheets

| Age | Recombinant embryo (N) | Fusion embryo (N) | 2-4 Cells (N) | Blastosphere (N) | % |
|---|---|---|---|---|---|
| 5 | 246 | 240 | 52 | 28 | 11.67 |
| 42 | 167 | 134 | 50 | 13 | 9.70 |
| 52 | 372 | 178 | 58 | 18 | 10.10 |
| 60 | 239 | 133 | 71 | 18 | 13.50 |

FIG. 9

EMBRYONIC STEM CELLS DERIVED FROM HUMAN SOMATIC CELL—RABBIT OOCYTE NT UNITS

TECHNICAL FIELD

The present Invention generally relates to the preparation of somatic cell derived embryonic stem cells (S-ES cells, also termed as nuclear transfer embryonic stem cells, ntES cells), or embryonic stem-like cells or other types of embryo-derived stem cells from nuclear transfer (nt) units (nt-units) at various implantation stages, by transplantation of human somatic cells or their nuclei into enucleated animal oocytes, and in a preferred embodiment the rabbit enucleated oocytes. The present invention more specifically relates to the preparation human ntES cells, embryonic stem-like cells or other types of embryo-derived stem cells by transplanting the human cells or cell nuclei into enucleated animal oocytes, more preferable leporid oocytes and most preferable enucleated New Zealand rabbit oocytes.

The present invention further relates to the use of ntES cells, embryonic stem-like cells or other types of embryo-derived stem cells in the induction of differentiated cells. ntES cells, embryonic stem-like cells, or other types of embryo-derived stem cells, either differentiated or non-differentiated, can be modified and used as cell carriers to introduce various types of bio-active molecules, including DNAs, RNAs or protein etc., into the human body. ntES cells, embryonic stem-like cells, or other types of embryo-derived stem cells, both modified and unmodified, can be used in the production of all kinds of differentiated cells, tissues and organs for the treatment and diagnosis of diseases. Also, the cells, of which the genes have been changed or unchanged, can per se be used as nuclear donors in the nuclear transplantation.

BACKGROUND OF THE INVENTION

The nuclear transplantation involves the transplantation of donor cells or cell nuclei into enucleated oocytes. The resultant nt-units can develop to various pre-implantation stages, or further into life-borne animals. This method was shown to be successful when applied to amphibians at the end of the 1950s. Briggs and King obtained nuclear transferred frogs by transferring nuclei of the enteric epithelium of the rananigromaculata into oocytes. Nuclear transfer had not been applied to mammals until the end of 1980s. Many types of somatic cells were used in the nuclear transfer experiments as the nuclear donor cells, including embryo blastomeres, inner cell mass, and terminal embryo cells in nuclear transfer (Collas et al., Mol. Reprod. Dev., 38:264-267, 1994; Keefer et al., Biology of Reproduction, 50:935-939, 1994; Sims et al., PNAS, 90:6155-6159, 1993).

Using adult sheep mammary gland as donor cell, Wilmut et al. in Britain (Nature 1997, 385, 810-813) produced the first living lamb from somatic cell nuclear transfer. In 1998, sequential mice somatic cells nuclear transplantation into was successfully completed in US (Wakayama, et al. Nature 394: 369-374, 1998). In 1999, nuclear transplantation of mice embryonic stem cell (ES) was completed (Teruhiko et al., PNAS 96:14984-14989, 1999). The success of nuclear transplantation using adult somatic cells is not only a progress in technique but also a progress in concept, showing the possibility that highly differentiated adult somatic cell nuclei can form new individuals once being reprogrammed to reenter development In 1999, Dominko et al. injected somatic cell nuclei from various animals (e.g. cows, sheep, pigs, monkeys, and rats) into bovine oocytes to develop nt-units, each developing to some extent (Biology of Reproduction. 60 (6): 1496-1502, 1999). These experiments show that mammalian somatic nuclei can be activated by oocytes of a species different from the nuclear donor to form nt-units. Such nt-units can develop to all the pre-implantation stages. The finding, that oocytes of one species can reprogram somatic nuclei of another species, shows that mechanisms controlling reprogramming are highly conserved in different mammalian species.

The advancement in ES cell cultivation has been also highlighted all over the world these years while the development of the nuclear transfer technology is flourishing. The basic manipulation involved in the establishment of ES cell and the basic characters and the application thereof have been well known in the art since the establishment of the mice ES cell line in 1981 (See Evans, et al. Nature, 29: 154-156, 1981; Martin, et al. PNAS, 78: 7634-7638, 1981). The ES cell can be kept in an undifferentiated, infinitely proliferating state. providing that the cultivation thereof is effected in a feeder layer of fibroblast cells (Evans, et al.) or under differentiation inhibiting conditions (Smith, et al. Development Biology, 121:1-9, 1987).

ES cells have the potential of development into all cell types of a body, including germ cell. ES cells can be differentiated to various specific cell types under appropriate induction conditions. Embryonic stem cells have been successfully directed to differentiate in vitro into various types of cells, e.g. the hematopoletic stem cells (Ronald, et al. PNAS, 92: 7530-7534, 1995), neural cells (Dinsmore, et al. Theriogenology, 49: 145-151, 1998), muscle cells (Reubinoff, et al. Nature Biotechnology, 18 (4): 399-404, 2000), adipocytes (Dani C Smith, et al. J Cell Sci, 110: 1279-1285, 1997), endothelial cells (Vittet, et al. Blood, 88 (9): 3424-3431, 1996) and so on. A specific cell type, e.g. a muscle-like cell, differentiated from ES cells display properties similar to that of its natural equivalent cell types, e.g. a muscle cell, therefore, cells differentiated from ES cell can be use in treatment of diseases (cell, tissue, or organ transplantation).

In view of the potentiality of the mouse ES cells, it has been tried to culture the ES cells of large mammals because the establishment thereof not only has the significance in scientific research but also can be applied to medicine. For example, the human ES cells can be directed to all kinds of specialized cells for the treatment of diseases. Because of their proliferation and differentiation potential, ES cells provided a platform for genetic modification. ES cells of large animals can be genetically modified to produce various biological products.

Isolation of ES cells or embryonic stem-like cells from large mammals have been reported. For example, Notarianni, et al. (J. Reprod. Fert., Suppl. 43: 255-260, 1991) reported that the cells in primary cultures of inner cell masses from pig and sheep blastocysts exhibit some morphological and growth characteristics similar to ES cells. Chen R L, et al. (Biology of Reproduction, 57 (4): 756-764, 1997) and Wianny, et al. (Theriogenology, 52 (2): 195-212, 1999) reported the isolation of pig ES cells from porcine blastocysts, respectively, Stekelenburg-Hamers, et al. reported the isolation and the characterization of embryonic stem-like cells from inner cell mass of bovine blastocysts (Mol. Reprod. 40: 444-454, 1995).

Thomson, et al. reported the successful isolation of ES cells from primate macaque (PNAS, 92 (17): 7844-8, 1995).

Thomson, et al. successfully established human ES cells lines (Science, 282 (6): 1145-1147, 1998), which is an important breakthrough in the stem cells research. These call lines not only can be used as important tools in the research of human development, but also has the broad application prospect in medical fields. For example, (1) human ES cells lines can be expanded and differentiated into specific cell types to meet the needs of the patients. They will become the cell source for cell or organ transplantation therapies. It is possible that many human diseases can be treated through cell transplantation. Besides its medical applications, (2) human ES cell lines may also facilitate the screen for new drugs and the safety evaluation of drugs.

However, the cells differentiated from the human ES cells may cause immune rejection while being used in the transplantation between the individuals of different MHC types, thus the patient would have to take immune inhibitor, which is toxic. At present, there is no method in obtaining ES cells that are compatible with the patient's immune systems by using his somatic cells.

Munsie, at al. reported the isolation of mice ES cells from blastocysts derived by somatic cell nuclear transfer (Current Biology 10: 989-992, 2000). Wakayama, et al. obtained the mice ES cells, which can be induced to various types of specific cells in vitro, from the cultures of blastocysts derived by somatic cell nuclear transfer (Science, 292 (5517); 740-743. 2001). The result of the research done by Wakayama, et al. demonstrates that ES cells can be isolated from nuclear transfer embryos by somatic cell nuclear transfer. The ntES cells of somatic cell origin are pluripotent and can differentiate into any specific cell types as ES cells derived from the normal zygote.

The successes achieved by all of these scientists mentioned above established a new route for treatment of the diseases, i.e., therapeutic cloning. It is suggested that somatic cells of the patient can be reprogrammed through nuclear transfer to produce ntES cells. The ntES cells obtained are further differentiated into the specific cell type needed by the patient. ntES cells and their differentiated progenies have the same genotype as the patient, and therefore would not be rejected by the patient's immune system when transplanted to the patient. Therapeutic cloning provides an approach to solve the problem of immune rejection commonly observed in transplantation medicine.

WO 98/07841 (Robe, et al., Massachusetts, U.S.A., filed in 1998) disclosed the isolation of the thirty 2-cell-stage embryos and six 4- to 16-cell-stage embryos and one 16- to 400-cell-stage embryo from the allogeneic nuclear transplantation from lymphocyte and mouth epithelium of human to the bovine oocytes. However, this study failed to provide any proof demonstrating that the embryos and cell colonies derived from the embryos were encoded by human genomic DNA rather than bovine genomic DNA. Blastocysts can be easily created through parthenogenesis of bovine oocytes. Furthermore, the patent application provided no proof demonstrating that the colonies were encoded by human genomic DNA and displayed any characteristics of human or primate stem cells, Up to the submission of the present application, there has been no report that the ntES cells can be obtained by human somatic cell nuclei transfer, neither the report that human specific cell types can be differentiated therefrom.

CONTENTS OF THE INVENTION

The present inventors discovered that nuclear transfer (nt) units (nt-units) could be obtained by transplantation of human cells, such as adult somatic cells or cell nuclei, into enucleated mammalian (including human) oocytes. The nuclear transfer embryonic stem cells (ntES cells) could be obtained from the nt-units at various pre-implantation stages. The ntES cells are similar in cellular characters and differentiation potential to that of the human ES cells obtained from the fertilized zygotes. The result was the first proof that human somatic cell nuclei might be reprogrammed after the transplantation into the enucleated oocytes. The result also proved that the human embryonic stem cells could be derived from nt-units at the blastocyst stage.

The result further proved the feasibility of cross-species nuclear transplantation, e. g. the transplantation of human cells or cell nuclei into the enucleated oocytes of a leporid animal, e.g. rabbit, to produce nt-units, which when cultured under appropriate conditions give rise to nt-units at various developmental stages encoded by the donor nuclei.

Therefore, it is an object of the invention to provide a method of obtaining ntES cells, embryonic stem-like cells or other types of embryo-derived stem cells. The method comprises reprogramming human somatic cell nuclei to obtain nt-units through nuclear transfer, and isolating ntES cells, embryonic stem-like cells or other types of embryo-derived stem cells from nt-units at various pre-implantation stages.

It is another object of the invention to provide improved methods for cross-species somatic cell nuclear transplantation.

It is a specific object of the invention to provide a novel method for producing ntES cells, embryonic stem-like cells or other types of embryo-derived stem cells, involving the transplantation of the cells or cell nuclei of a mammalian species (including human) into enucleated oocytes of a species different from the nuclear donor.

It is another object of the invention to provide a novel method for producing human ntES cells, embryonic stem-like cells or other types of embryo-derived stem cells, involving the transplantation of the cells, e.g. human adult somatic cells or cell nuclei into enucleated oocytes of the same species, e.g. human oocytes.

It is another object of the invention to produce human ntES cells, embryonic stem-like cells or other types of embryo-derived stem cells by transplantation of human cells or cell nuclei into enucleated oocytes, e.g. enucleated leporid oocytes.

It is another object of the invention to provide a novel method for producing ntES cells, embryonic stem-like cells or other types of embryo-derived stem cells, involving the transplantation of the cells or cell nuclei of a human into enucleated oocytes, e.g. enucleated rabbit oocyte.

It is a more specific object of the invention to obtain ntES cell lines that could proliferate without limiting in a similar way to the embryonic stem cells obtained from fertilized embryos, which should express all the special markers of the primate ES cells, and have the potential to differentiate to all kinds of cells of ectoderm, mesoderm, and endoderm.

It is a specific object of the invention to obtain the ntES cell lines, which are compatible to the immune system of the nuclear donor. The ntES cells and the cells, tissues and organs derived from ntES cells are encoded by the genome of the nuclear donor, Thus, transplantation of the ntES cells or cells, tissues and organs derived from ntES cells back into the nuclear donor, e.g. the patient, will not cause immune rejection.

It is a more specific object of the invention to differentiate human ntES cells, embryonic stem-like cells or other types of embryo-derived stem cells directionally to specific type cells including muscle cells, neural cells, fibroblasts and adipocytes in a specific inductive environment, including in vivo and in vitro inductive system.

It is another specific object of the invention to use the human ntES cells or embryonic stem-like cells or other types of embryo-derived stem cells and their differentiated progenies for the treatment and diagnosis of diseases.

It is another specific object of the invention to use human ntES cells, embryonic stem-like cells or other types of embryo-derived stem cells and their differentiated progenies for construction of differentiated human tissues or organs.

It is another object of the invention to provide human ntES cells, or embryonic stem-like cells, or other types of embryo-derived stem cells or differentiated cells, tissues or organs derived through somatic cell nuclear transfer for transplantation therapies. Such therapies include by way of examples the treatment of diseases and injuries, including but not limited to Parkinson's syndrome, Huntington's syndrome, Alzheimer's syndrome, ALS, spinal cord injuries, multiple sclerosis, muscular dystrophy, diabetes, liver disease, heart disease, cartilage replacement, burns, vascular disease, urinary tract disease, as well as the treatment of immunodeficiency diseases, bone marrow transplantation, cancer, etc.

It is another specific object of the invention to use the human ntES cells, embryonic stem-like cells or other types of embryo-derived stem cells and their differentiated progenies as cell carriers for the transport of all kinds of bio-active molecule, modified DNA, RNA or protein etc. into the human body. The cells, modified or unmodified, may be used for the preparation of all kinds of differentiated cells, tissues and organs for use in medical therapies, including the treatment and diagnostic of diseases.

It is another object of the invention to use human ntES cells, embryonic stem-like cells or other types of embryo-derived stem cells and their differentiated progenies in the treatment of various diseases, in particular for the treatment and/or prevention of the diseases and injuries specified, supra.

It is another object of the invention to use genetically modified human ntES cells, embryonic stem-like cells or other types of embryo-derived stem cells and their differentiated progenies as nuclear donors in the nuclear transplantation.

It is another specific object of the invention to use human ntES cells, embryonic stem-like cells or other types of embryo-derived stem cells and their differentiated progenies for the study of cell differentiation and for drug screening and toxicity evaluation.

With the foregoing and other objectives, advantages and features of the invention that will become hereinafter apparent, the nature of the invention may be more clearly understood by reference to the following detailed description of the preferred embodiments of the invention and to the appended claims.

BRIEFS DESCRIPTION OF THE FIGURES

FIG. 9 is a table showing somatic cells from donors at different ages formed blastocysts with comparable efficency.

DETAILED DESCRIPTION OF THE INVENTION

Figure 1:
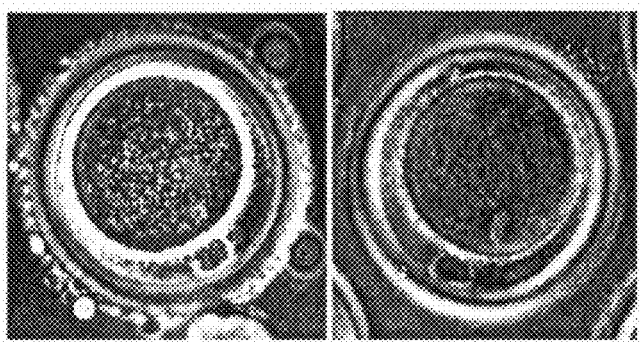
FIG. 1 is a photograph of the rabbit oocytes.

In the present invention, nuclear transfer (nt) and nuclear transplantation are used interchangeably.

In the present invention, somatic embryo and nt-unit are used interchangeably.

In the present invention, nuclear transfer embryonic stem cell (ntES cell) and somatic cell derived embryonic stem cell (S-ES) are used interchangeably.

The term "nuclear transplantation" referred herein means the transplantation of donor cells or cell nuclei into enucleated oocytes. The resultant nt-units are cultured to various pre-implantation stages (e.g. blastocyst) or are allowed to further develop into live-bone non-human animals. For nuclear transfer, cells or cell nuclei of human or animals, for example, animals of primates, ungulates, amphibians, rodents species, can all be used as nuclear donors. Human oocytes may be used in nuclear transplantation, as well as oocytes from other species, including those derived from primates, ungulates, amphibians, rodents, etc.

The term "homogeneous nuclear transplantation" referred herein means the transplantation of donor cells or cell nuclei into enucleated oocytes from the same species. The resultant nt-units are cultured to various pre-implantation stages or allowed to further develop into live-borne animals.

The term "nuclear transplantation in different species" referred herein means the transplantation of donor cells or cell nuclei into enucleated oocytes of a species different from the nuclear donor. The resultant nt-units are cultured to various pre-implantation stages or allowed to further develop into live-borne animals.

The term "nuclear transfer (nt) unit (nt-unit)" referred herein means a unit derived from the combination of a nuclear donor and an enucleated oocyte. The nuclear donor and the enucleated oocyte may be obtained from the same species or from different species.

The term "somatic embryo" reffered herein means nt-units at various pre-implantation stages, including the 2-cell stage, 4-cell stage, 8-cell stage, morula stage, blastocyst stage, and hatching blastocyst stage.

The term "somatic cell" referred herein means all cells types in an adult body except the germ cells.

For mammalian species, a zygote develops through the 2-cell stage, 4-cell stage, 8-cell stage, morula stage, blastocyst, hatching blastocyst in sequence. Inner cell mass located in a blastocyst is the founder of the embryo proper, which will give rise to all cells of the embryo. ES cells are the equivalent of cells of the inner cell mass, therefore are pluripotent, capable of development to any of the cells of the growing fetus including the germ line.

Human ES cell derived from the inner cell mass is a type of pluripotent stem cells which can be induced to differentiate into any cell types, including germ line cells, and is permanent in vitro. In a long-term culture, these cells maintain a normal karyotype. The cells express the special markers: negative for SSEA-1 and positive for SSEA-3, SSEA-4, TRA-1-60, TRA-1-81. They are positive for alkaline phosphatase.

Human nuclear transfer embryonic stem cells, obtained by transplantation of human cell nuclei into non-human mammalian oocytes, have properties similar to ES cells isolated from the fertilized zygote. Human ntES cells can be propagated infinitely in vitro and maintain a normal karyotype. These cells can be induced to differentiate into cells of all three germ layers. Undifferentiated human ntES cells express markers typical of primate ES cells, which are negative for SSEA-1 and positive for SSEA-3, SSEA-4, TRA-1-60, TRA-1-81, and are positive for alkaline phosphatase.

The term "embryonic stem-like cells" referred herein means the cell-mass derived from nt-units at greater than the 2-cell stages that has part of the characters of the human embryonic stem cells as above.

The term "other types embryo-derived stem cells" referred herein means all cells derived from nt-units at various pre-implantation stages except embryonic stem cells and embryonic stem-like cells. The term "specialized cells" referred herein means the cells differentiated from ntES cells, embryonic stem-like cells and other types of embryo-derived stem cells, which can be induced artificially to differentiate in vivo or in vitro.

The present invention provides a method of preparing the ntES cells, embryonic stem-like cells or other types of embryo-derived stem, cells, comprising the following steps:

(i) transplanting nuclear donor cells or cell nuclei into enucleated oocytes to form nt-units;

(ii) activating the obtained nuclear transfer units;

(iii) culturing the nuclear transfer units to various pre-implantation stages; and (iv) obtaining nuclear transfer embryonic stem cells, embryonic stem-like cells or other types of embryo-derived stem cells coded by the donor nuclei from the nt-units greater than 2-cell development stage.

The present invention provides a further method of inducing the ntES cells into many types of specific cells, comprising the following steps:

(i) preparing embryonic stem cells or embryonic stem-like cells or other types of embryo-derived stem cells from reprogrammed somatic cells by nuclear transfer; and (ii) inducing the above cells to differentiate to specialized cells under appropriate condition.

In a preferred embodiment, an appropriate small animal, such as a rabbit, is used as an oocyte donor for nuclear transfer. By maintaining these animals in appropriate animal houses, they could be fed with standard food and would be more easily administered, thus resulting in a lower cost. Moreover, it would be easier to control these rabbits free from diseases and being SPF (specific pathogen free). Four days after injection of a rabbit with artificial hormone, about 30 oocytes can be obtained for the nuclear transfer experiment. Rabbit nature estrus period is 7-9 days.

The present inventors discovered that a nuclear transfer unit could be obtained by transplantation of the nuclei of human cells, specifically human fibroblasts, into enucleated rabbit oocytes to obtain nt-units at various developmental stages.

In view of the fact that human cell nuclei can be effectively reprogrammed by rabbit oocytes, it is reasonable to expect that human somatic cells may be transplanted into oocytes of other non-rabbit animal species (e.g. ungulates) to obtain nu-units. Oocytes from other animal sources should also be suitable. For example, oocytes derived from non-human primates, amphibians, rodents, etc. Further, using similar methods, it should be possible to transfer human cells or nuclei into human oocytes and use the resultant blastocysts to produce ntES cells.

Therefore, in its broadest sense, the present invention involves the transplantation of human or animal cells or cell nuclei into enucleated oocytes of a species different from the nuclear donor to obtain nt-units for isolating embryonic stem cells or embryonic stem-like cells or other types of embryo-derived stem cells. For example, the invention may involve the transplantation of human cells or cell nuclei into enucleated oocytes of another species (e.g. a rodent) to produce nt-units, which can develop to nt-units at various pre-implantation stages, including those at the morula stage, blastocytes, and hatching blastocytes stages. nt-units at various pre-implantation stages are useful for isolation of embryonic stem cells, embryonic stem-like cells or other types of embryo-derived stem cells for therapeutic cloning.

The present inventors discovered that nuclear transfer units can be obtained by transplantation of human somatic cell nuclei into enucleated animal oocytes to produce nt-units at the blastocyst stage. ntES cells can then be isolated from nt-units at the blastocyst stage. These results demonstrate that the blastocysts obtained from cross-species nuclear transplantation have the capability to give rise the embryonic stem cell lines as the embryos derived from fertilized zygotes.

ntES cell lines from cross-species nuclear transfer can be cultured on feeder cell layers for a long period of time, and can passage for more than 30 passages. Cells obtained thereby have not only the capability of differentiation into all three germ layers, including ectoderm, mesoderm, endoderm, but also the capability of differentiating to many kinds of specialized cells including muscle cells, adipocytes, nerve cell and fibroblast etc.

These discoveries are of great importance in solving the problem of immune rejection in medical transplantation. As well known in the art, new organs, cells or tissues can be used to replace or reverse the functions of the original organs, cells or tissues when they could not function properly. For example, the kidney transplantation can be effected if a kidney cannot do function normally, and hematopoietic stem cells from other human are used to replace the exhausted hematopoietic stem cells in the therapy of the tumor. It has been a serious problem in the medical transplantation for several decades that the organs, cells or tissues transplanted into the patients would be rejected by the immune system of the recipient, because of the mismatch in MHC genes between the organ donor and recipient. In recent years, scientists put forward a conception of therapeutic cloning targeting for solving the immune rejection. The somatic cells could be reprogrammed by nuclear transplantation in order to obtain nt-units for isolating ntES cells. ntES cells can then be induced to differentiate into the, organs, tissues or cells needed by the patient, and transplanted back into the patient.

Since the resultant cells, tissues or organs are encoded by the patient's own genome and will most likely be recognized as "self", transplantation of cells, tissues and organs resulting from therapeutic cloning should not cause immune rejection. The present inventors discovered the following in the invention:

(i) ntES cell lines can be obtained from human somatic cell nuclei by somatic cell nuclear transfer.

(ii) ntES cell lines can proliferate in vitro for long time as conventional human ES cells derived from fertilized zygotes.

(iii) nt cells have the potential to differentiate into cell types of all 3 germ layers, including ectoderm, mesoderm, endoderm. These discoveries demonstrate that therapeutic cloning is practically feasible. The present inventors further discovered that human somatic cell could be reprogrammed effectively by the oocyte of a non-human mammalian species, preferably the oocyte of rabbit.

Therefore, in the broadest sense, the present invention involves the transplantation of human or animal cells or cell nuclei into enucleated oocytes of a species different from the nuclear donor to obtain nt-units at various pre-implantation stages for isolating ntES cells.

Human Cell Nuclear Transfer Technique

Nuclear transfer technique or nuclear transplantation techniques have been described in many references, such as some of the references cited in the background of the invention (See in particular, Wilmut, et al., Nature 385:810-813, 1997; Campbell, et al., Biology of Reproduction 49 (5): 933-942, 1993; Collas, et al., Mol. Reprod. Dev, 38:264-267, 1994; Keffer, et al., Biology of Reproduction, 50:935-939, 1994; Sims, et al., PNAS, 90:6155-6159, 1993; and Patents NOs WO 94/26884, WO 94/24274, and WO 90/03432, which are incorporated by reference in their entirety herein.

Nuclear Donor

In the invention, the cells used as donors for nuclear transfer are derived from human cells, preferably human fibroblasts.

Human or animal cells, preferably somatic cells, may be obtained and cultured according to the methods known in the art. Human and animal cells useful in the present invention include, by way of examples, epithelial cells, neural cells, epidermal cells, keratinocytes, hematopoletic cells, melanocytes, chondrocytes, lymphocytes (B and T lymphocytes), nucleated erythrocytes, macrophages, mononuclear cells, fibroblasts, cardiac muscle cells, and other muscle cells. Moreover, the human cells used for nuclear transfer may be obtained from different organs, for instance, the skin, lung, pancreas, liver, stomach, intestine, heart, reproductive organs, bladder, kidney, and urethra and other urinary organs. Suitable donor cells (i.e., cells useful in the subject invention) may be obtained from any cell or organ of the body, including all somatic cells.

Oocytes

The oocytes used for nuclear transfer may be obtained from various animals, including mammals and amphibians. Suitable mammalian sources for oocytes include sheep, cattle, pigs, horses, rabbits, guinea pigs, mice, hamsters, rats, primates, etc. In a preferred embodiment, the oocytes will be obtained from a leporid source, most preferable from a rabbit.

Mature metaphase II stage oocytes can be collected surgically from the reproductive tract of non-superovulated or superovulated rabbits 14 to 24 hours after onset of estrus or the injection of human chorionic gonadotropin (hCG) or a similar hormone, with the optimal time being 15 to 18 hours.

Methods for isolation of oocytes are well known in the art. Essentially, the method comprises isolating oocytes from the ovaries or reproductive tract of a mammal or amphibian, e.g. a rabbit.

The degree of maturation of the oocyte in nuclear transfer has been reported to be a major factor in the success of the nuclear transfer methods (see, Prather et al., Differentiation, 48, 1-8, 1991). In general, previous successful mammalian animal cloning practices use the metaphase II stage oocytes as the recipient oocyte because at this stage it is believed that the oocyte can effectively "activate" the introduced nucleus to initiate and develop to animal embryos.

Enucleating

It has been discovered in the present invention that mature oocytes obtained from New Zealand rabbits should be enucleated 15 to 23 hours after the injection of hCG. Prior to enucleating, the oocytes will be placed in M2 culture medium (Sigma) containing hyaluronidase. Cumulus cells will be removed by repeated pipetting through pipettes very small inner diameter or by vortexing briefly. The stripped oocytes are then screened for those contain polar bodies, and the selected metaphase II oocytes, as confirmed by the presence of polar bodies, are then used for nuclear transfer, enucleating.

Generally, immature oocytes collected from animal ovaries should be matured in vitro as desired, until they are in the metaphase II stage.

For New Zealand rabbits, enucleating should be performed not more than 20 hours past the injection of hCG, with 16 to 18 hours being preferable.

Enucleating may be accomplished micro-surgically using a micropipette to remove the polar body and the adjacent cytoplasm. The efficiency of enucleating may be examined by staining the removed polar body and chromatin with Hoechst 33342 dye, and observed DNA under ultraviolet irradiation rapidly.

nt-Unit Preparation nt-units may be prepared according to the methods known per se in the art, e.g. by injection into the zona pellucid and by injection into the cytoplasm.

Injection into the Zona Pellucid:

A single animal or human cell or cell nucleus, which is typically of a species different from that of the enucleated oocyte, will be transferred into the perivitelline space of the latter. Preferably, the nt-unit, consisting of a human or animal cell and a rabbit oocyte, will be electrofused in a 0.5 mm chamber by 1-2 applications of an electrical pulse of 90-120V for about 60 μsec each or more frequently in electrofusion medium (e.g. mannitol, sucrose or sorbitol fusion medium) 16 to 20 hrs after the injection of hCG. After fusion, each fused nt-unit will be placed in a suitable tissue culture medium, e.g. RD {DEME (Gibco): RPMI-1640 (Gibco)}; M199 (Gibco), DMEM (Gibco), until incubation.

Electrofusion is accomplished by providing a pulse of electricity sufficient to cause a transient breakdown of the plasma membrane. Essentially, if two adjacent membranes are induced to break down, the lipid bilayers will intermingle and small channels will open between the two cells after the membranes reform. Due to the thermodynamic instability of such a small opening, it enlarges until the two cells fuse into one, Reference is made to U.S. Pat. No. 4,997,384 by Prather et al. (incorporated herein by reference in its entirety), which provides a further discussion of the process. A variety of electrofusion media can be used, including, e.g. sucrose, mannitol, sorbitol and phosphate buffered solution. Fusion can also be accomplished by using Sendai virus as a fusogenic agent.

According to the present invention, the nt-units may be activated by known methods, including culturing the nt-units at sub-physiological temperature, essentially by applying a cold temperature shock to the nt-units. This may be most conveniently done by culturing the nt-units at room temperature, which is low relative to the physiological temperature conditions to which embryos are normally exposed.

Suitable oocyte activation methods are the subject of U.S. Pat. No. 5,496,720 by Susko-Parrish et al., which is herein incorporated by reference.

Oocyte activation may be effected sequentially:
(i) increasing levels of divalent cations in the oocyte, and
(ii) reducing phosphorylation of cellular proteins in the oocyte.

The methods of increasing divalent cation levels include, for example, the addition of kinase inhibitors, e.g. the serine-threonine kinase inhibitors 6-dimethyl-amino-purine, staurosporine, 2-aminopurine, and sphingosine.

Alternatively, phosphorylation of cellular proteins may be inhibited by the introduction of a phosphatase into the oocyte (e.g. phosphatase 2A or phosphatase 2B).

Injection into the Cytoplasm:

Other methods may be used for nuclear transplantation, including injecting the nucleus directly into the oocyte cytoplasm rather than using electroporation. These techniques are applicable only when the nucleus of the donor somatic cell are able to be reprogrammed by the oocyte, which in turn must be capable of inducing a human somatic cell reprogrammed in rabbit oocyte cytoplasm. (Collas and Barnes, Mol. Reprod. Dev, 38:264-267, 1994).

nt-Unit Culturing

An activated nt-unit may be cultured in a suitable culture medium for further development. For example, activated nt-units may be transferred into and micro-cultured in medium RD, M199, DMEM50, 50 microliter of culture medium being covered by a layer of paraffin, e.g. at 38° C. and 5% $CO_2$. In one of the preferable examples, the highest rate of blastocysts was obtained by culturing nt-units in RD medium.

According to the inventor's experience, for human cell/enucleated rabbit oocyte derived nt-units, the blastocyst will be obtained about 6-7 days after initiation of oocyte activation. nt-units will typically exhibit appearance and cellular characters similar to embryos of the nuclear donor species rather than the oocyte donor species. For example, in the case of a nt-units obtained by the transfer of a human nuclear donor cell into an enucleated rabbit oocyte, the development of the nt-unit follows a schedule more typical of a human rather than a rabbit embryo. It takes approximately 6-7 days to form a blastocyst, unlike a rabbit embryo, which usually forms a blastocyst in approximately 3-4 days.

The media used for tissue culture and for maintaining rabbit embryos include DMEM+15% FBS; M199+15% FBS; and RD+15% FBS. In addition, they can be used for co-culture with a variety of cell types, including granulose, oviduct, uterine, and STO cells.

ntES Cell Line Establishment:

The culture system is the most important factor in the ntES cell line establishment. The system includes the mediums and the feeder layers. The mediums mean a liquid suitable for ntES cells culturing, including as a ingredient DMEM (Gibco); FBS (Hyclone); non-essential amino acid stock (Gibco); β-mercaptoethanol; Knockout medium (Gibco); SR (Gibco); and various factors.

The first type of the factors is the ligand of glucose-protein 130, e.g. LIF (R&D), which, together with the gp-130, may initiate the pathway of signal transduction.

The second type of the factors is the endogenous cAMP agonist, e.g. Forskoline (Sigma), preferably at 10 μM.

The third type of the factors is the growth factor, e.g. bFGF (R&D), which may inhibit the apoptosis of the ES cells.

The feeder layers mean the fibroblasts obtained from the 13.5 days' mouse embryo. They may sustain the ntES cells' growing after inactivation by Mitomycin C (Sigma). In a preferred embodiment, the feeder cells comprise mouse embryonic fibroblasts. The preparation of a suitable fibroblast feeder layer will be described in the examples below.

The human ntES cells line was successfully obtained from the nt-units using the above culture system. The human ntES cell colonies have a longer doubling time than the mouse ES cells, and exhibit colony appearances and growth characters similar to human ES cells rather than mouse ES cells.

The human ntES cells obtained according to the present invention sustain the high positive for alkaline phosphatase (Sigma) after a long term of culture, over 30 passages. They also express the surface markers in common with the primate ES cells, e.g. SSEA-1 (−), SSEA-3 (+), SSEA-4 (+), TRA-1-10 (+), and TRA-1-81 (+). This shows that the ES cells sustain growth in an undifferentiated state.

The human ntES cells obtained according to the present invention in colonies are centralized and compacted, and cells arranged closely, with bigger nucleus and less cytoplasm. They have the same growth characters as the primate ES cells as follows:
(i) sustaining growth in an undifferentiated state in vitro,
(ii) maintaining normal karyotype during a long term of culturing, and
(iii) capable of developing into specific cell types of 3 germ layers, including ectoderm, mesoderm, and endoderm.

Induction and Differentiation:

Thomson, et al. (Science, 282 (6), November; 1145-1147, 1998) reported the successful establishment of the human ES cell line using the blastocysts remained from IVF. Then they also demonstrated that the human ES cells and the cells derived therefrom had the capability of forming the embryold body (ED) and derivatives of all three embryonic germ layers, including ectoderm, mesoderm, and endoderm.

Wakayama, et al. (Science, 292 (5517): 740-743, 2001) reported the successful isolation of the mouse ES cells from the blastocyst by somatic cell nuclear transfer. The ES derived by somatic cell could be induced to all kinds of specific cells in vitro. His experiment proved the blastocyst from nuclear transfer has the same use of deriving the ES cells as the normal blastocyst. The ntES derived by somatic cell had the fully pluripotency, capable of developing into an integral adult and all cell types contained therein.

The invention provides a method to produce the ntES cells by nuclear transfer. The studies conducted by the inventors demonstrate that the human ntES cells have the same capabilities, like the normal ES cells derived; forming the embryold body and differentiate to all three embryonic germ layers (e.g. ectoderm—neurofilament, NSE: mesoderm—myoD, myoglobin, desmin, vWF; endoderm—α-anti-trypsin, α-fetoprotein molecular markers positive).

The invention provides various conditions for inducing human ntES cells to differentiate, including inducing both in vitro and in vivo. The induction in vitro can be separated into (A) self-induction, which involves the induction of the ntES cells or ntES-like cells automatically under the specific culturing conditions, and (B) the biochemical induction, which involves putting the ntES cells or ntES cells into the mediums comprising retinoic acid or beta-mercaptoethanol (Sigma) or DMSO or $H_2O_2$ for the first stage and then replacing the medium with other special medium to promote the cells differentiation.

Induction in vivo involves putting the human ntES cells directly or indirectly, after being induced in vitro, into the special parts of animal or human and inducing them to differentiate, The Prospects of ntES Cell:

The human ntES cells, embryonic stem-like cells or other types of embryo-derived stem cells obtained from the nt-units in the present invention could be used in the therapy of many diseases/many therapeutic usages.

In principle, the ntES cells may be used to obtain any desired differentiated cell type. Therapeutic usages of such differentiated human cells are unparalleled. For example, human hematopoietic stem cells may be used in medical treatments requiring bone marrow transplantation, and human neural stem cells may be used in regenerative medicine for spinal cord injuries and Parkinson's disease.

Other diseases and conditions treatable by isogenic cell therapy include, by way of example, multiple scleroses, muscular dystrophy, diabetes, liver diseases, heart diseases, cartilage replacement, burns, foot ulcers, gastrointestinal diseases, vascular diseases, kidney diseases, urinary tract diseases, and aging related diseases and conditions.

The human ntES cells or the derived cells thereof produced according to the present invention may be used as cell carriers to transport all kinds of extrinsic bio-functional material into human body. Transfer the DNA, RNA protein or other bio-functional materials into the ntES cells or its derived cells thereof by the methods of transgene, homologous gene recombination, transposon plasmid transfection, virus transfection, etc, and then transfer the ntES cells or the derived cells thereof into the human body, thus the DNA, RNA and protein transferred can play a role in vivo.

By using the method as described above, the defective genes, e.g. defective immune system genes, cystic fibrosis genes can be replaced, or the genes which can express therapeutically beneficial proteins such as growth factors, lymphokines, cytokines, enzyme, etc, can be introduced. For example, the gene encoding brain growth factors may be introduced into human embryonic stem cell or the derived cells of other types and then the differentiated or undifferentiated cells genetically modified may be transplanted into a patent suffering from Parkinson's disease to treat the disease.

Using such methods, desired genes may be introduced into the subject ntES cells, and the cells will differentiate into needed cell types, e.g. hematopoietic cells, neural cells, pancreatic cells, cartilage cells, etc, and then the resultant cells or the cells derived therefrom can be used in the therapy.

Genes which may be introduced into the subject ntES cells include, by way of example, epidermal growth factor, basic fibroblast growth factor, glial derived neurotrophic growth factor, insulin-like growth factor (I and II), neurotrophin-3, neurotropphin-4/5, ciliary neurotrophic factor, AFT-1, cytokine genes (interleukins, interferons, colony stimulating factors, tumor necrosis factors (alpha and beta), etc.), genes encoding enzymes etc.

The subject ntES cells also may be used as the controlling genes and for the study of genes, which are involved in the regulation of early development to find out the important factors in the process of cell differentiation. Abnormity differentiation and division of cells caused many serious diseases and congenital malformationare. Therefore, in-depth studies on the process of differentiation, division and induction of the normal cells will provide a clear understanding of the cells pathological process of those diseases.

Also, differentiated cells tissues and organs from the subject ntES cells may be used in the development of drugs. The study on the embryonic stem cells will greatly change the methods of producing drugs and safety examination for drugs. The embryonic stem cells may differentiate varied cells to be used in studying, screening and identification of the drugs. In future drug research, only the experimental drugs, which have passed the ES cell experiment in vitro, could be used on the experimental animal or used in the clinical experiment on human.

In addition, nuclear xeno-transplantation techniques may be used to save the species close to extinction, such as the giant panda. In these species, larger numbers of female oocytes are hardly to obtain as the number of the female is less. Their somatic cell may therefore be transplanted into enucleated oocytes of different species. The resultant nuclear transfer units would then be cultured in vitro to obtain blastocysts, which could then be transplanted into the pregnant mother to develop a normal individual.

In order to more clearly describe the invention, the following examples are provided.

EXAMPLE 1

The Preparation of Nuclear Donor Cells for Nuclear Transfer

Foreskin tissue obtained from surgery with informed consent was minced and washed with PBS, centrifuged at 1000 rpm for 5 minutes, digested by 0.05% Trypsin/0.02% EDTA (Gibco) at 37° C. for 30 minutes. Remove excessive solution from the tube and centrifuge the tube at 1000 rpm for 5 minutes. Discard the supernatant and culture the cell pellet in 90% DMEM (Gibco)+10% FBS (Hyclone)+50 IU/ml penicillin-streptomycin (Gibco). Re-suspend in plate and incubate at 37° C., 5% $CO_2$, with the medium changed every 3 days. Passage after the cell grows to confluent and the cells of the $7^{th}$-$20^{th}$ passage are used as nuclear donor cells (FIG. 1).

Oocyte Preparation

Figure 2:
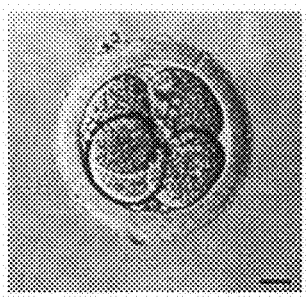
FIG. 2 is a photograph of the nt-unit (obtained by injection of a somatic cell into the zona pellucid) at the 4-cell stage
Figure 3:
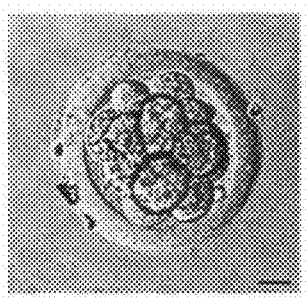
FIG. 3 is a photograph of the nt-unit (obtained by injection of a somatic cell into the zona pellucid) at the morular stage.
Figure 4:
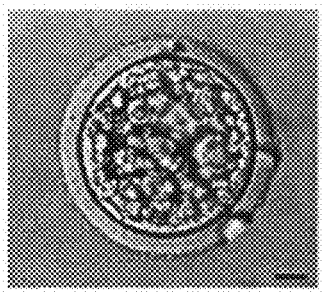
FIG. 4 is a photograph of the nt-unit (obtained by injection of a somatic cell into the zona pelucid) at the biastocyst stage.
Figure 5:
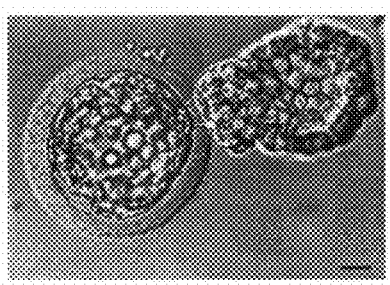
FIG. 5 is a photograph of the nt-unit (obtained by injection of a somatic cell into the zona pellucid) at the hatching biastocyst stage.
Figure 6:
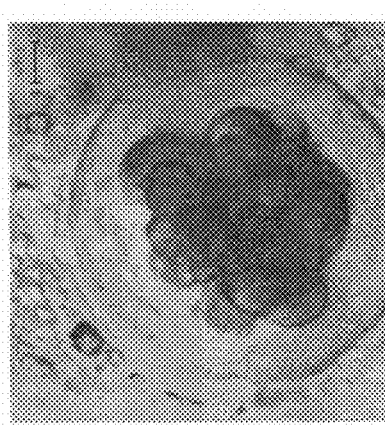
FIG. 6 is a photograph of the nt-unit (obtained by injection of the somatic cell into the cytoplasm of the oocyte) at the morula stage.
Figure 7:
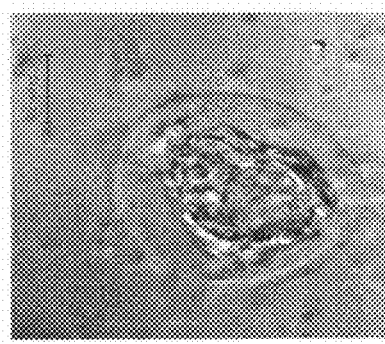
FIG. 7 is a photograph of the nt-unit (obtained by injection of the somatic cell into the cytioplasm of the oocyte) at the blastocyst stage.
Figure 8:
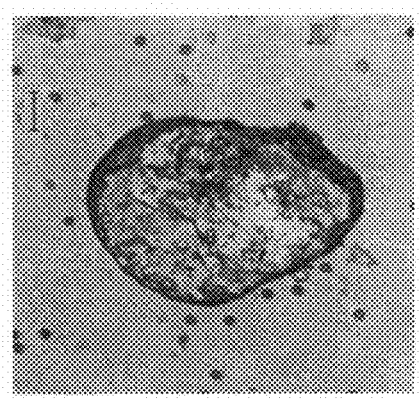
FIG. 8 is a photograph of the nt-unit (obtained by injection of the somatic cell into the cytoplasm of the oocyte) at the hatching blastocyst stage.
Figure 10:
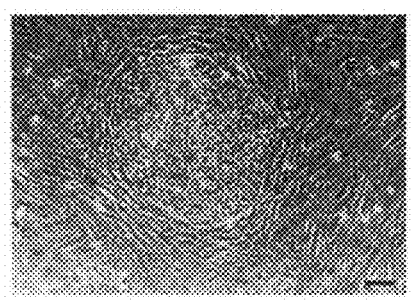
FIG. 10 is a photograph of a ntES cell colony derived from human somatic cells reprogramed by a rabbit oocyte.
Figure 11:
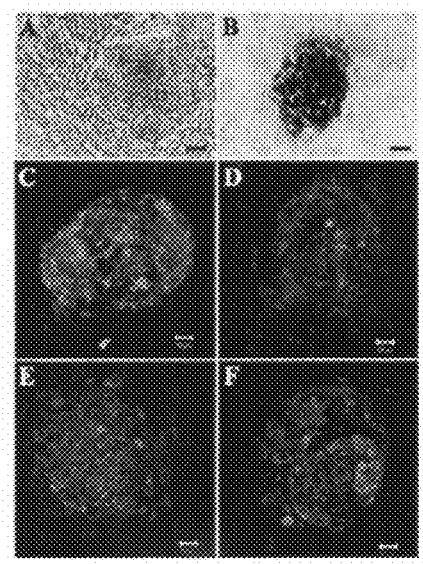
FIG. 11 is a photograph of a ntEs cell colony drived by human somatic cell nuclear transfer, express markers typical of primate Es cells, and high alkaline phosphatase activity.

Mature New Zealand female Rabbit, 2.5-3 kg, was superovulated with a single dose injection of 100 IU PMSG (i.m.) (The first bio-pharmaceutical company, Shanghai), followed by a single dose injection of 100 IU hCG (HuaFu High Bio-Technology Company, Tlanjing) (i.v.) 72 hours later. Mature oocytes were flushed out of the oviducts 14-16 hours after hCG injection using pre-warmed M2 solution (Sigma) Oocytes were put into a solution containing 300 IU/ml hyaluronidase to remove cumulus cells. The oocytes (FIG. 2) were then washed in M2 solution for 3 times.

Nuclear Transfer Procedures

Injection into the Zona Pellucid:

Oocytes were manipulated in M2 medium with 7.5 μg/ml Cytochalasin B (Sigma) and incubated and enucleated by a needle with a bevel after maintained for 10 minutes at room temperature. After that, put the single donor fibroblast into the perivitelline space of enucleated rabbit oocyte, forming nt-units. The nt-units were equilibrated in a fusion buffer solution containing 0.3 M Glucose (Sigma); 0.1 mM $MgCl_2$ (Sigma); 0.05 mM $CaCl_2$ (Sigma) and stimulated with a single direct current pulse of HV 120V for 60 μsec. After stimulation, the nt-units were incubated in RD medium, consisting of DMEM 42.5% (Gibco), RPMI-1640 42.5% (Gibco), and 15% FBS (Hyclone). After 6-7 days, blastocysts were obtained (FIGS. 3-6, 11).

Injection into the Cytoplasm

Oocytes were incubated in M2 solution with 7.5 μg/ml Cytochalasin B (Sigma) and enucleated by a needle with a bevel after maintained for 10 minutes at room temperature. After that, put the single donor fibroblast into the cytoplasm of the enucleated rabbit oocyte, forming a nt-unit. Many nt-units were cultured in RD medium, consisting of DMEM 42.5% (Gibco), RPMI-1640 42.5% (Gibco), 15% FBS (Hyclone). After 6-7 days, blastocysts were obtained (FIGS. 7-10).

EXAMPLE 2

Establishing Human Nuclear Transfer Embryonic Stem Cells Lines nt-units at the blastocyst stage were obtained as described above and pipetted up and down gently using a glass needle (stretched from a glass pipe of 3 mm diameter) with a diameter smaller than the blastocyst to strip zona pellucid. Then, the inner cell masses of the blastocysts were isolated and plated onto feeder layers and cultured in 79% DMEM (Gibco), 20% FBS (Hyclone), 1% non-essential amino acid stock (Gibco), 0.1 mM β-mercaptoethanol (Gibco), 10 ng/ml LIF (R&D), 10 ng/ml bFGF (R&D), 10 μM Forskolin (Sigma) at 37° C. in 5% $CO_2$, with half of the medium changed every 2 days.

Figure 12:
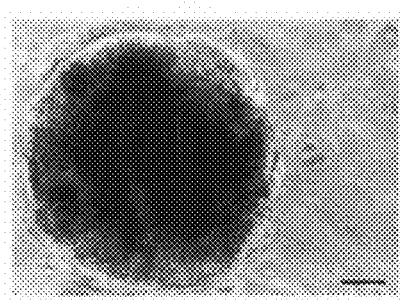
FIG. 12 shows that ntEs cells are capable of forming an embryoid body by somatic cell nuclear transfer.

After 2-4 days' culturing, cell mass was observed to be growing on the feeder. After 7-20 days, colonies were observed (FIG. 12). The colonies were dispersed by enzyme or mechanical and passed onto a plate containing fresh feeder layer. After 20 passages, the ntES cells were cryopreserved.

Fibroblast Feeder Layer

The feeder cells were derived from mouse embryos of 14-16 days old. After the removal of the head, liver, heart and esophagus of the embryos under sterile condition, the remains of the embryo were minced, digested in a pre-warmed solution containing 0.05% Trypsin/0.02% EDTA (Gibco), incubate at 37° C. for 30 minutes, centrifuged at 1000 rpm for 5 minutes. The cells pellet was re-suspended in 90% DMEM (Gibco); 10% FBS (Hyclone); 50 IU penicillin-streptomycin (Gibco), plated and incubated at 37° C., 5% $CO_2$. After passage 3 times, a feeder layer was treated with 10 mM Mitomycin C (Sigma) for 3-4 hours and passed on 4-well or 96-well plate. A feeder layer grew in a 37° C. humidified incubator containing 5% $CO_2$. The plates with homogenous feeder layer were used to prepare S-ES Culture.

Charicterization of ntES Cells

Primate ES cells express alkaline phosphatase activity, and can express a series of characteristic surface antigens, and therefore they can be identified by detecting Alkaline phosphatase activity and the immunohistochemistry of SSEA-1, SSEA-3, SSEA-4, TRA-1-10, TRA-1-81 antibodies.

Method of detecting Alkaline phosphatase activity: The ES cells cultured on 4-well plate were fixed with 4% paraformaldehyde for 5 minutes, and were washed with PBS for 3 times. Then, added the substrate of alkaline phosphatase (Sigma) to the well, and stay at dark for 15 minutes. ntES cells expressed a high level of alkaline phosphatase activity, but the mouse feeder cells are negative. (FIG. 13).

Immunohistochemical method: Plated the ES cells onto a plastic glass slide, then fixed with 4% paraformaldehyde for 5 minutes, washed with PBS for 3 times, then added the 1:5 to 1:25 antibody dilutions of SSEA-1, SSEA-3, SSEA-4, TRA-1-10, TRA-1-81 (available from Developmental Hybridoma Bank, Iowa City, Iowa) to the wells respectively, stayed at room temperature for 1 hour, washed with PBS 2 times, add second antibody-FITC, stay at RT for 30 minutes, washed with PBS for 2 times, added the second antibody labeled with FITC and cultured for 30 mins, and examined by a laser confocal microscope.

Figure 13:
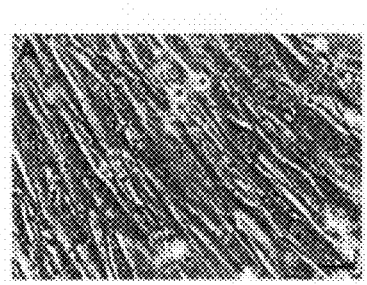
FIG. 13 is a photograph of muscle cells differentiated from human ntES cells by somatic cell nuclear transfer.

The result of 5 different antibodies detected: 4 are positive (FIG. 13).

| Antibody | SSEA-1 | SSEA-3 | SSEA-4 | TRA-1-10 | TRA-1-18 |
|---|---|---|---|---|---|
| Result | − | + | + | + | + |

Karyotyping

Figure 17:
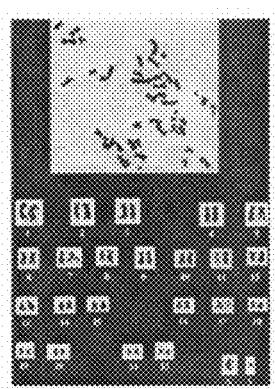
FIG. 17 is a photograph of the karyotype of the ntEs cell of the $26^{th}$ passage.

Put 10 μg/ml Colchicine in cell cultures. After 37° C. for 4 hours, the cells were removed out from the plate and centrifuged cells at 1000 rpm for 8 minutes. Discard the supernatant, re-suspend cell pellet in pre-warmed 0.05M KCl, and incubate at 37° C. for 30 minutes. Centrifuge at 1000 rpm for 8 mins, Discard the supernatant, re-suspend cell pellet in a fixation solution (methanol:ice acetic acid=3:1) and keep at room temperature for 15 minutes. Centrifuge at 1000 rpm for 8 minutes, Discard the supernatant, and re-suspend cells pellet again in a fixation solution at room temperature for 15 minutes. After centrifuging at 1000 rpm for 8 minutes, put cell pellet into a glass plate and stain with GIEMSA to examine the karyotype. One of he results is shown in FIG. 17.

EXAMPLE 3

Induction of Early Muscle Cells Differentiation

Figure 15:
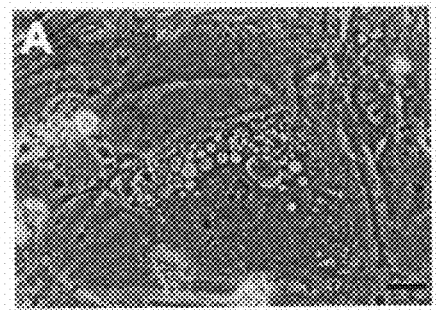
FIG. 15 is a photograph showing that ntES cells are capable of differentitiating into cells expressing markers of all three germ layers.

Culture the EB or EB-like cell mass in the RA medium containing DMEM (Gibco), 0.5 μm retinoic acid (Sigma), 10% FBS (Hyclone) for 5 days. After replacing the medium with the muscle cell culture medium containing 79% DMEM (Gibco), 10% FBS (Hyclone), 10% Horse Serum (Sigma), 1% chick embryo extract (Gibco), culture further 7-10 days, can become muscle-like cell. The cells arrange in parallel, some of which have several nucleus (FIG. 15).

EXAMPLE 4

Inducution of Neuron Differentiation

Figure 16:
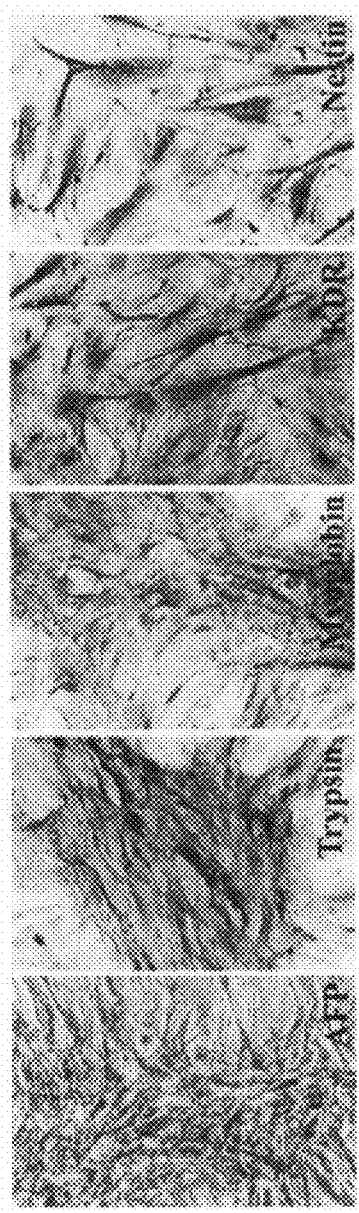
FIG. 16 is a photograph showing that ntES cells are capable of differentiating into cells expressing markers of all three germ layers.

Culture the EB or EB-like cell mass in the RA medium containing DMEM (Gibco), 0.5 μm retinoic acid (Sigma), 10% FBS (Hyclone) for 5 days. After replacing the medium with the neuron culture medium which containing DMEM-F12 (Gibco), 1% ITS (Gibco), culture further for 7-10 days, the EB or EB-like cell can become into neuron cells with some filamentous projections stretching out from the cell body (FIG. 16).

EXAMPLE 5

Induction of Fibroblasts-Like Differentiation

Culture the EB or EB-like cell mass in the RA medium containing 90% DMEM (Gibco), 0.5 μm retinoic acid (Sigma), 10% FBS (Hyclone) or the neuron culture medium which containing DMEM-F12 (Gibco), 1% ITS (Gibco), or the muscle cell culture medium containing 79% DMEM (Gibco), 10% FBS (Hyclone), 10% Horse Serum (Sigma), 1% chick embryo extract (Gibco), the EB or EB-like cell can become into fibroblasts-like cells. The cells are flat and polymorphous with big nucleus and dear nucleolus, and rich cytoplasm (FIG. 17).

EXAMPLE 6

Induction of Adipocyte Differentiation

Culture the EB or EB-like cell mass in the RA medium containing 90% DMEM (Gibco), 0.5 μm retinoic acid (Sigma), 10% FBS (Hyclone) for several days, the EB or EB-like cell can become into adipocytes (FIG. 15). The cells dyed by Oil Red O, an adipocyte-specific dye, are confirmed to be adipocytes containing fat drop in the cytoplasm.

EXAMPLE 7

Preparation of EB

Figure 14:
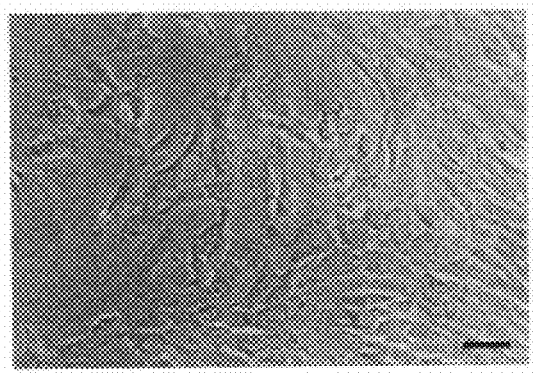
FIG. 14 is a photograph of fibroblast lile cells differentiated from human ntES cells by somatic cell nuclear transfer.

Culture ntES cells in the ES cell medium containing 79% DMEM (Gibco), 20% FBS (Hyclone), 1% non-essential amino acid stock (Gibco), 0.1 mM β-mercaptoethanol (Gibco), 10 ng/ml LIF (R&D), 10 ng/ml bFGF (R&D), 10 μM Forskolin (Sigma) at 37° C., 5% $CO_2$ for more than 7-14 days, a portion of ntES cells underwent spontaneous differentiation and formed EB (FIG. 14).

EXAMPLE 8

Identification of Three Germ Layers

Identify the EB or EB-like cell mass by an immunohistochemical method.
Ectoderm marker antibody: positive for nestin (Chemicon).
Mesoderm marker: positive for myoglobin (Dako) and KDR (Sigma).
Endoderm marker: positive for α-fetoprotein (BioGenex), α-anti-trypsin (Dako).
The results suggested that the cell mass differentiated from EB or EB-like cell mass contained the cells derived from all three germ layers cells (FIG. 19).

While the present invention has been described with reference to the specific embodiments thereof, it should be understood by those skilled in the art that various changes and modification may be made without departing from the true spirit and scope of the invention. All such modifications are intended to be within the scope of the description and the claims appended hereto.

The invention claimed is:
1. A method of preparation of embryonic stem cells by somatic cell nuclear transfer, comprising the following steps:
 (i) providing a human donor cell or cell nucleus;
 (ii) providing an enucleated rabbit oocyte;
 (ii) transplanting the human donor cell or cell nucleus into the enucleated oocyte to obtain an nt-unit;
 (iii) activating the obtained nt-unit;
 (iv) culturing the activated nt-unit to obtain a blastocyst; and
 (v) culturing the inner cell mass of the blastocyst with bFGF to produce embryonic stem cells express alkaline phosphatase, undergo at least 30 passages, form cells of all three embryonic germ layers and express the cell surface markers of human ES cells.

2. The method of claim 1, wherein said oocyte is in the middle of a divisional period.

3. The method of claim 1, wherein said oocyte is enucleated within 24 hours after injection of human chorionic gonadotropin into a female rabbit.

4. The method of claim 1, wherein the obtained nt-unit is activated by culture at room temperature or by using an activating agent.

5. The method of claim 1, wherein the obtained nt-unit is electrofused in an electrofusion solution selected from the group consisting of mannitol electrofusion solution, sucrose electrofusion solution, sorbitol electrofusion solution and phosphate buffered solution.

6. The method of claim 1, wherein the activated nt-unit is cultured in a medium selected from the group consisting of RD medium, M 199 medium, and DMEM medium to obtain an nt-unit at a pre-implantation stage.

7. The method of claim 1, wherein the activated nt-unit is cultured in medium selected from the group consisting of RD medium, M 199 medium, and DMEM medium, and on feeder cells to form a co-culture system to obtain an nt-unit at a pre-implantation stage.

8. The method of claim 1, wherein an nt-unit at a greater than 2-cell development stage are cultured to isolate ntES cells.

9. The method of claim 1, wherein the medium used to culture the ntES cells is DMEM medium, or knockout medium so as to maintain the ntES cells in an undifferentiated state.

10. The method of claim 9, wherein the medium contains one or more other factors.

11. The method of claim 10, wherein the other factors are selected from the group consisting of Leukemia Inhibitor Factor (LIF), basic fibroblast growth factor (bFGF) and Forskolin.

12. The method of claim 2, wherein the oocyte is in the middle of the metaphase II stage.

13. The method of claim 5, wherein the electrofusion solution is a sucrose electrofusion solution.

14. The method of claim 6, wherein the medium is the RD medium.

15. The method of claim 7, wherein the feeder layer comprises STO mouse fibroblast cells.

16. The method of claim 9, wherein the medium used to culture the ntES cells is DMEM medium.

17. The method of claim 1, further comprising screening the embryonic stem cells for expression of alkaline phosphatase, undergoing at least 30 passages, formation cells of all three embryonic germ layers and expressing the cell surface markers of human ES cells.

* * * * *